United States Patent [19]
Winocur

[11] Patent Number: 5,100,227
[45] Date of Patent: Mar. 31, 1992

[54] TRANSLATION INSENSITIVE KERATOMETER USING MOIRE DEFLECTOMETRY

[76] Inventor: Joseph Winocur, 14 San Ramon, Irvine, Calif. 92715

[21] Appl. No.: 603,992

[22] Filed: Oct. 26, 1990

Related U.S. Application Data

[63] Continuation-in-part of Ser. No. 384,159, Jul. 21, 1989, Pat. No. 4,984,883.

[51] Int. Cl.⁵ .............................................. A61B 3/10
[52] U.S. Cl. .................................... 351/212; 351/247
[58] Field of Search ............... 351/211, 209, 210, 212, 351/247; 356/35.5, 376

[56] References Cited

U.S. PATENT DOCUMENTS

| | | | |
|---|---|---|---|
| 4,432,239 | 2/1984 | Bykov | 356/35.5 |
| 4,692,003 | 9/1987 | Adachi et al. | 351/212 |
| 4,850,693 | 7/1989 | Deason et al. | 356/35.5 |

*Primary Examiner*—Rodney B. Bovernick
*Attorney, Agent, or Firm*—Roy A. Ekstrand

[57] ABSTRACT

An improved translation insensitive keratometer includes a pair of optical coupling systems for irradiating a specular object having different beam geometries. Laser beams are separately identified by a unique identifying characteristic and processed through the optical coupling systems to a plurality of moire deflectometers.

37 Claims, 3 Drawing Sheets

TRANSLATION INSENSITIVE KERATOMETER USING MOIRE DEFLECTOMETRY

CROSS REFERENCE TO RELATED APPLICATION

This application is a continuation-in-part of copending application Ser. No. 07/384,159, filed July 21, 1989 now U.S. Pat. No. 4,984,883 and entitled Translation Insensitive Keratometer Using Moire Deflectometry which is filed in the name of the Applicant of the present application and which is hereby incorporated herein by reference.

FIELD OF THE INVENTION

This invention relates generally to measurement of curved specular objects and particularly to keratometry as used to measure cornea shape.

BACKGROUND OF THE INVENTION

A conventional moire deflectogram produced by light reflected from the anterior surface of the cornea is sensitive to both the radius of curvature of the anterior cornea surface and the distance of a compensating lens form the anterior surface of the cornea. In such systems, it is necessary to make an independent measurement of the position of the compensating lens in order to evaluate the radius of curvature of the cornea. In accordance with the keratometer set forth in the above-referenced parent application, two probe light beams are used to make two independent deflectogram measurements of the cornea. As a result of the invention therein, the position of the compensating lens and the radius of curvature of the anterior surface of the cornea can be determined simultaneously without independent measurement.

Because the above-referenced parent application sets forth a single system geometry, and because additional geometries may be found beneficial in certain environments, there remains a need in the art for additional systems for keratometry which remain translation insensitive.

SUMMARY OF THE INVENTION

Accordingly, it is a general object of the present invention to provide an improved translation insensitive keratometer. It is a more particular object of the present invention to provide an improved system of keratometry which utilizes a variety of geometries. In accordance with the present invention, there is provided for use in measuring the curvature and shape of a specular object having a curved surface and a radius of curvature, a keratometer comprises: first, second and third moire deflectometers; first, second and third video cameras directed to said first, second and third moire deflectometers respectively; a source of collimated light; a beam expander coupled to said source of collimated light; first optical transmission means having a first beam identifier and coupling the output of said beam expander to the specular object having a first identifying characteristic such that the incident light thereon is focused at the radius of curvature of the specular object and such that the light reflected from said specular object is received by said first and second moire deflectometers; second optical transmission means having a second beam identifier and coupling the output of said beam expander to said specular object having a second identifying characteristic such that the incident light thereon is focused at the curved surface of the specular object.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

DESCRIPTION OF THE PREFERRED EMBODIMENTS

Figure 1:
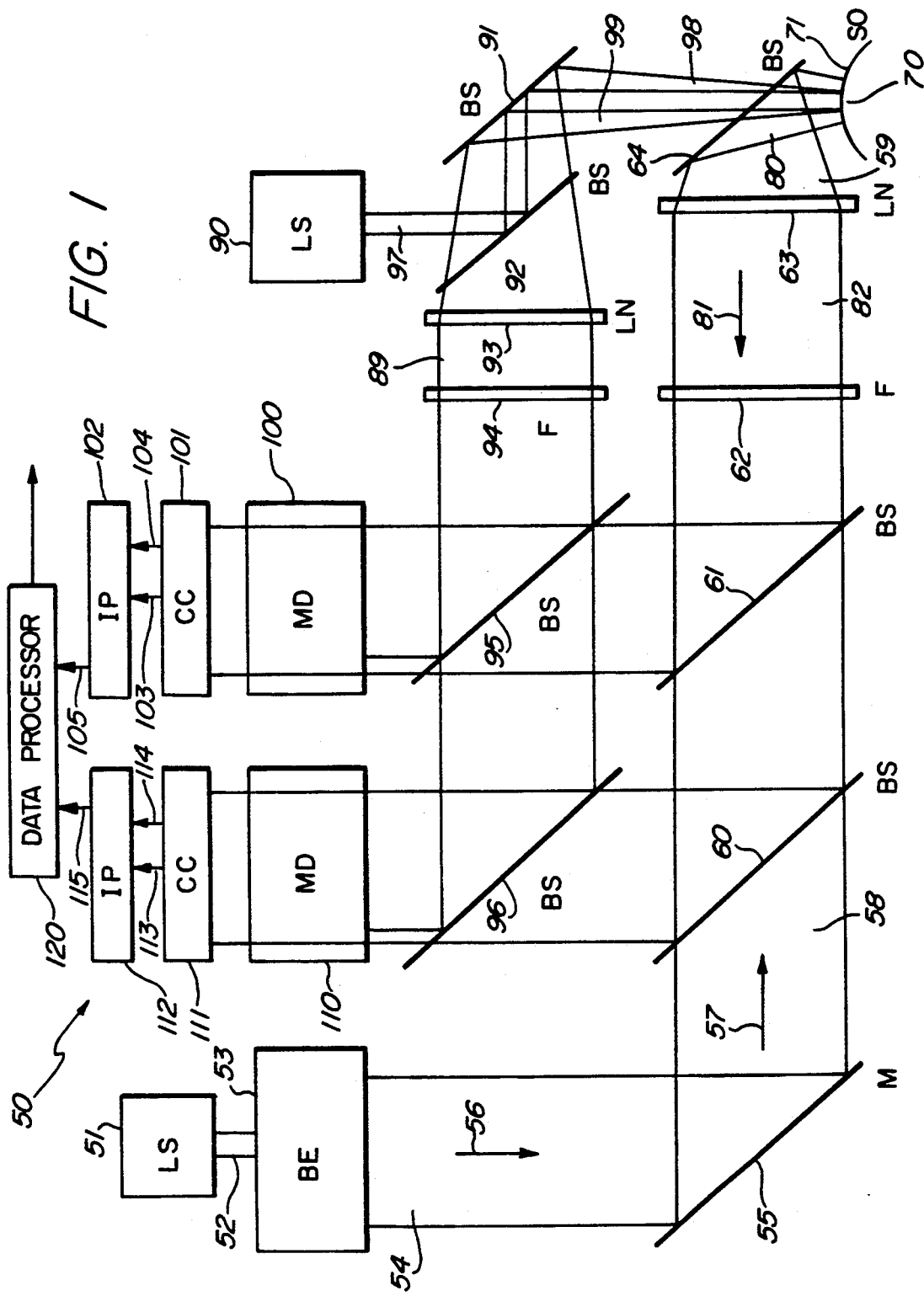
FIG. 1 sets forth a schematic diagram of a translation insensitive keratometer using moire deflectometry shown as FIG. 3 in the above-referenced parent application.

FIG. 1 sets forth a schematic diagram of the keratometer set forth in the above-referenced patent application. As is set forth therein FIG. 3 sets forth a translation insensitive keratometer using moire deflectometry constructed in accordance with the present invention and generally referenced by numeral 50. Keratometer 50 includes a laser 51 and a beam expander 53. Laser 51 produces a single wavelength light beam 52 which is expanded by beam expander 53 to form an expanded beam 54. Beam expander 53 is directed toward an angled mirror 55 which reflects expanded beam 54 to a reflected beam 58 directed in the direction indicated by arrow 57. A pair of angled beam splitters 60 and 61 are positioned within the path of reflected beam 58 such that beam 58 passes through beam splitters 60 and 61. A filter 62 having a predetermined filter characteristic is positioned within the path of light beam 58 downstream of beam splitters 60 and 61. A converging lens 63 is positioned in the path of reflected beam 58 downstream of filter 62 and converges beam 58 to a converging light beam 59. A beam splitter 64 is positioned in the path of converging light beam 59 and relfects light beam 59 as reflected beam 80. A specular object 70 having a reflective surface 71 is positioned within the path of reflected beam 80.

A moire deflectometer 100, constructed in accordance with conventional moire deflectometry construction and a charge coupled device TV camera 101, are optically coupled such that the output of moire deflectometer 100 is imaged by camera 101. An image processing system 102 is coupled to camera 101. A second moire deflectometer 110 and a second charged coupled device TV camera 111 are coupled such that camera 111 images the output of moire deflectometer 110. An image processing system 112 is coupled to camera 111. A pair of beam splitters 95 and 96 are positioned beneath moire deflectometers 100 and 110 respectively and in general alignment. A transmission filter 94 having a predetermined filter characteristic is aligned with beam splitters 95 and 96. A converging lens 93 is positioned in alignment with filter 94. A laser 90 producing a collimated beam of light 97 having a predetermined wavelength different from light beam 52 of laser 51 and a pair of beam splitters 92 and 91 cooperate to direct light beam 97 to surface 71 of specular object 70.

In operation, light beam 52 produced by laser 51 is expanded by beam expander 53 to form expanded beam 54 which travels in the direction indicated by arrow 56 to impinge mirror 55. Beam 54 is reflected from mirror 55 to form a reflected light beam 58 travelling in the direction indicated by arrow 57. Beam 58 passes through beam splitters 60 and 61 and is filtered by transmission filter 62. Thereafter, beam 58 is converged by lens 63 to form a converging beam 59 which is reflected by beam splitter 64 to impinge surface 71 of specular object 70. The spherical character of surface 71 imparts a divergent character to reflected beam 80 which is partially reflected by beam splitter 64 back through lens 63. Lens 63 collimates reflected beam 80 to form a collimated reflected beam 82 travelling in the direction indicated by arrow 81. Reflected beam 82 passes through filter 62 and is partially reflected by beam splitter 61 passing through 95 to be received and analyzed by moire deflectometer 100. Moire deflectometer 100 in turn produces a moire deflectogram which is received by camera 101 and processed by image processing system 102. The portion of reflected beam 82 transmitted through beam splitter 61 is reflected by beam splitter 60 and transmitted through beam splitter 96 to impinge moire deflectometer 110. Moire deflectometer 110 in turn produces a moire deflectogram which is imaged by camera 111 to produce an image signal which is processed by image processor 112. It should be noted that in accordance with an important aspect of the present invention the grating screens of moire deflectometer 110 are oriented orthogonal to those of moire deflectometer 100. As a result, the deflectograms produced by moire deflectometers 100 and 110 in processing reflected beam 82 simultaneously produce the orthogonally related moire deflectograms required for dynamic testing and measurement.

Laser 90 produces a small collimated light beam 97 which is partially reflected by beam splitter 92 to impinge beam splitter 91 and be partially reflected therefrom once again as reflected beam 98 which passes through beam splitter 64 to impinge surface 71 of specular object 70. Beam 98 is reflected from spherical surface 71 of object 70 as a divergent beam 99 which passes through beam splitter 64 and is reflected from beam splitter 91 and thereafter transmitted through beam splitter 92. The divergent beam passing through beam splitter 92 is collimated by lens 93 to form a collimated beam 89 which passes through transmission filter 94 and is partially reflected by beam splitter 95 to impinge moire deflectometer 100. The portion of beam 89 passing through beam splitter 95 is partially reflected by beam splitter 96 to impinge moire deflectometer 110. The images produced by moire deflectometers 100 and 110 in response to beam 89 are received by cameras 101 and 111 respectively and converted to electronic signals which are processed by image processors 102 and 112.

It should be noted that filter 62 has a filter characteristic permitting transmission of the wavelength of light produced by laser 51 but preventing transmission of the wavelength of light produced by laser 90. Conversely, the filter characteristics of filter 94 are selected to provide transmission of the output light of laser 90 while preventing transmission of the output light produced by laser 51. The wavelengths of light produced by lasers 51 and 90 are chosen to correspond to two different primary colors of cameras 101 and 102 such as blue and red, blue and green, or green and red. The charge coupled device color TV cameras 101 and 111 produce different signals for each primary color received which are then processed by image processors 102 and 112 respectively. Thus, the output signals of cameras 101 and 111 comprise separate moire deflectograms for moire deflectometers 100 and 110 respectively for each of the light signals processed from lasers 51 and 90.

The calculations underlying the described keratometer are set forth in the above-referenced parent application.

Figure 2A:
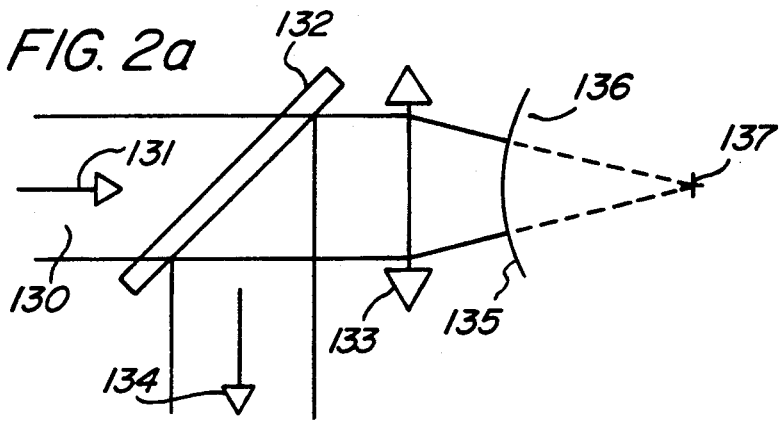
FIGS. 2(a) through 2(d) set forth partial schematic diagrams of beam geometries for the present invention translation insensitive keratometer using moire deflectometry.
Figure 2B:
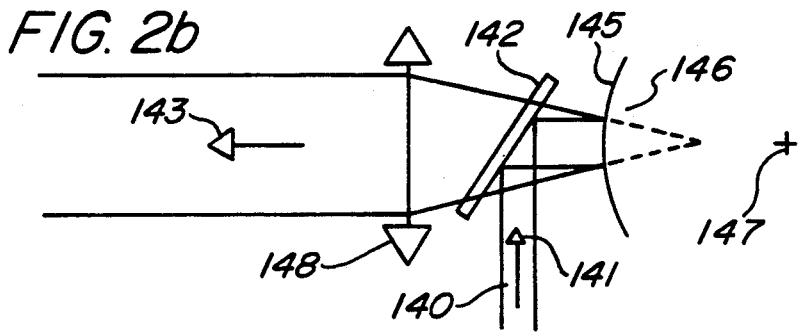

FIGS. 2(a) and 2(b) set forth simplified schematic drawings of the geometries used in the previously described keratometer. Additional beam geometries are set forth in FIGS. 2(c) and 2(d).

Specifically, and with reference to FIGS. 2(a) and 2(b), a laser beam 130, traveling in the direction indicated by arrow 131 is focused by lens 133 at the center of curvature 137 of the front surface 135 of the cornea 136. The beam is reflected from the front surface of the cornea and is collimated by lens 133 and partially reflected from beam splitter 132. This partially reflected collimated beam, traveling in the direction indicated by arrow 134, impinges a moire deflectometer (not shown). FIG. 2(b) shows a collimated laser beam, 140, traveling in the direction indicated by arrow 141, partially reflected from beam splitter 142. The partially reflected beam is reflected from the front surface 145 of the cornea 146. The reflected beam diverges as if it had originated from a point one-half of the distance from the front surface of the cornea 145 to the center of curvature of the cornea, 147. This divergent beam is collimated by lens 148. This collimated beam, traveling in the direction indicated by arrow 143 can then be made incident on a moire deflectometer, not shown.

Figure 2C:
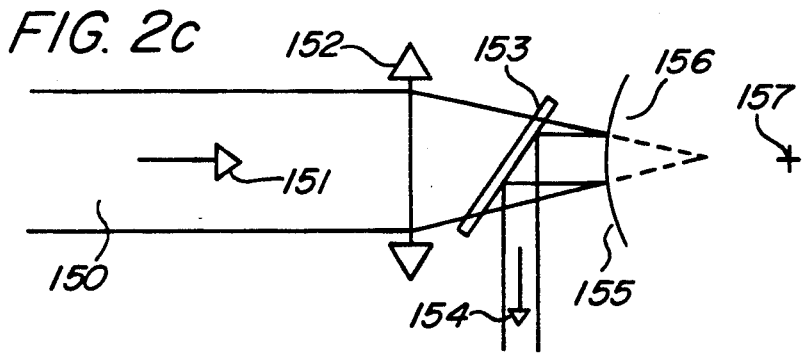
Figure 2D:
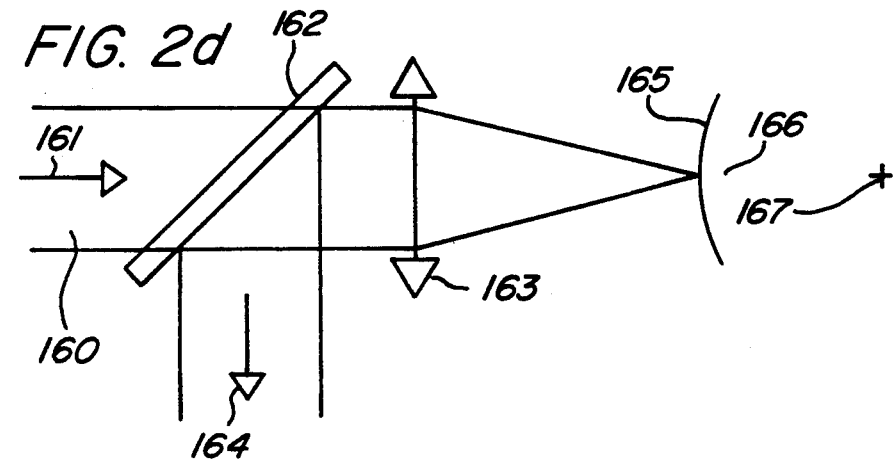

FIGS. 2(c) and 2(d) illustrate alternate useful beam geometries.

FIG. 2(c) shows a collimated laser beam, 150, traveling in the direction indicated by arrow 151, focused by lens 152 at a point one-half the distance from the front surface 155 of the cornea 156 to the center of curvature 157 of the front surface 155. The collimated reflected beam from the front surface of the cornea is partially reflected by beam splitter 153 and travels in the direction indicated by arrow 154. This collimated beam then impinges a moire deflectometer (not shown).

FIG. 2(d) shows a collimated laser beam, 160, traveling in the direction indicated by arrow 161, focused by lens 163 at the front surface 165 of the cornea 166. The reflected beam is collimated by lens 163 and partially reflected from beam splitter 162. This partially reflected collimated beam, traveling in the direction indicated by arrow 164 impinges a moire deflectometer (not shown).

As is set forth in the above-referenced parent application, the two laser beams shown in FIG. 1 (FIG. 3 of the parent application) are distinguished according to their color. The present invention, however, recognizes that other means of tagging or distinguishing two laser beams can also be used. For example, two independent orthogonal states of polarization such as linear horizontal and linear vertical or right and left circular can be generated by means of presently available light polarizers. In essence, a polarizer that produces one pure state of polarization inherently acts as a filter to reject the orthogonal state of polarization. Laser beams may also be rendered distinguishable by imposition of amplitude modulations of particular shapes, frequencies, and phases. Laser beam selection is then accomplished using a matched filter to pass the laser beam having the selected form of modulation etc. and to reject a laser beam having a different form of modulation etc. Laser beams may also be distinguished by using a time-shared common optical path. One method of time sharing involves pulsing the two beams on and off asynchronously. With this method, only one detector is required to detect both beams.

In summary, there are four single laser beam geometries which have been found appropriate for use in the present invention: The first, shown in FIG. 2(a), uses a collimated beam that is focused at the center of curvature of the cornea front surface. The second, shown in FIG. 2(b), uses a collimated beam that is reflected from the front cornea surface. The third, shown in FIG. 2(c), uses a collimated beam that is focused at one-half the radius of curvature of the cornea. The fourth, shown in FIG. 2(d), uses a collimated beam that is focused at the front surface of the cornea. These four beam geometries may be combined into six possible combinations of two different single laser beam geometries to form six different two beam systems. These combinations are:

(1): The first and second geometries;
(2): the first and third geometries;
(3): the first and fourth geometries;
(4): the second and third geometries;
(5): the second and fourth geometries; and
(6): the third and fourth geometries.

In addition, the above-described four different methods of beam identification may be used. These are (a) beam color, (b) beam polarization state, (c) modulation form, and (d) time sharing. Any combination of beam geometries and beam identification methods may be used to form alternate embodiments of the present invention keratometer. Thus, there are twenty four total possible combinations. It should be noted that the embodiment described in the above-referenced parent application uses a combination of the first and second beam geometries, that is, two beam system (1) above together with beam identification based upon beam color, that is, method (a).

Figure 3:
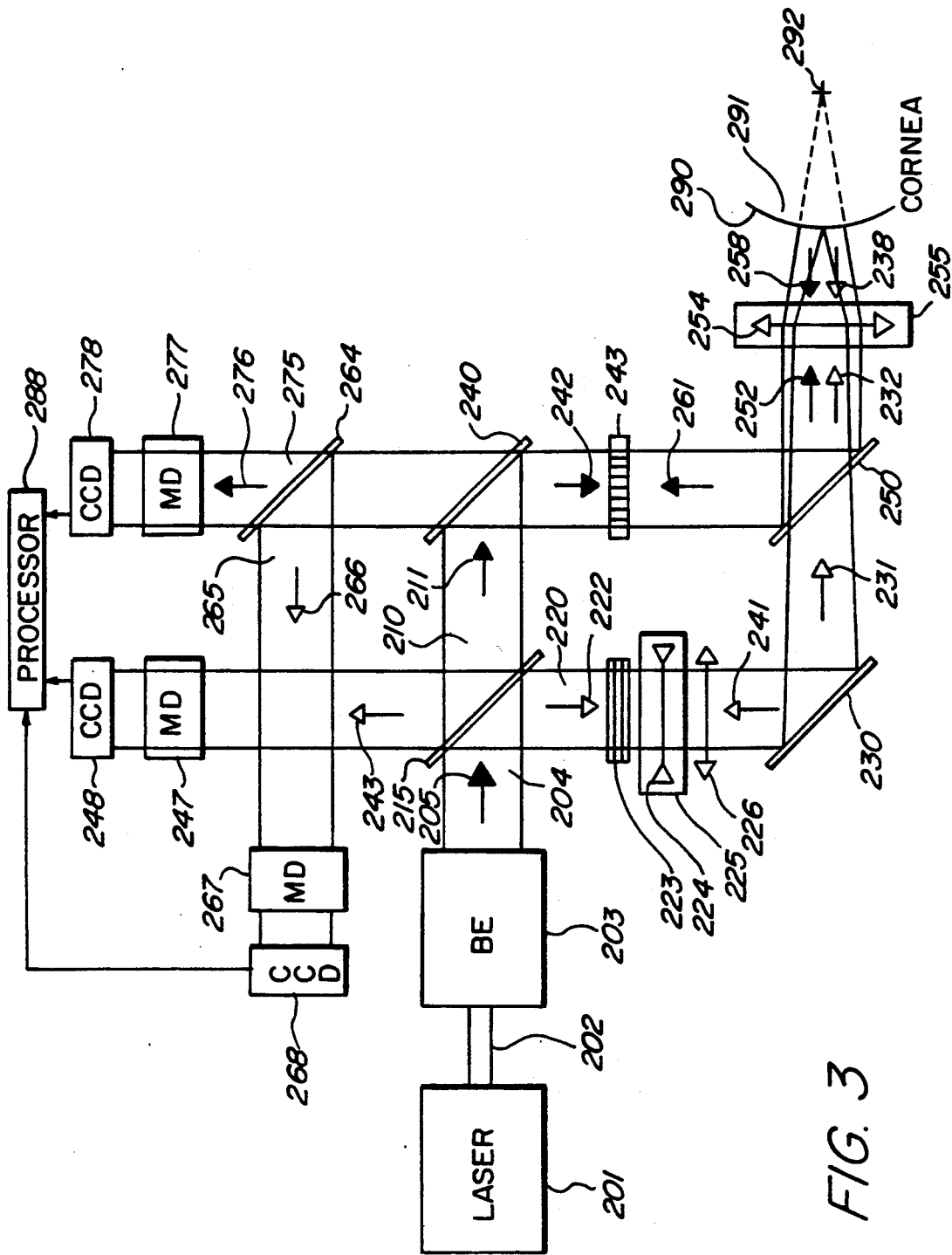
FIG. 3 sets forth a schematic diagram of a translation insensitive keratometer constructed in accordance with the present invention.

FIG. 3 sets forth a preferred embodiment of a translation insensitive moire keratometer that employs a combination of two beam system (3) and beam identification method (b), as defined previously. Specifically, in this embodiment of the invention, the first beam is focused on the center of curvature of the cornea, the second beam is focused on the center of the front surface of the cornea, and the two beams are identified by their orthogonal states of linear polarization. This invention is generally referenced here by numeral 200.

This specific embodiment of a translation insensitive moire keratometer, shown in FIG. 3, operates in the following manner. A light beam 202 produced by laser 201 is expanded by beam expander 203 to form expanded beam 204 which travels in the direction indicated by arrow 205 to impinge upon beam splitter 215. Approximately one-half of beam 204 is transmitted by beam splitter 215 and one-half is reflected. The transmitted beam, whose direction of travel is indicated by "light" arrows is focused at the center of curvature of the cornea. The reflected beam, whose direction of travel is indicated by "dark" arrows is focused at the front surface of the cornea. The optical paths of these beams, and the methods of their control, focus, detection and analysis are described below.

Consider first the transmitted beam, 210, traveling in the direction indicated by arrow 211. It is partially reflected from beam splitter 240 and travels in the direction indicated by arrow 242. This beam impinges on polarizer 243 which causes the light transmitted through it to be linearly polarized. Any direction of linear polarization may be chosen. To help make this presentation of the invention more explicit, let us assume that the vertical direction of polarization has been chosen. This vertically polarized light beam is partially reflected from beam splitter 250 and travels in the direction indicated by arrow 252. Next it impinges on converging lens 254 to form a converging beam focused at the center of curvature 292 of the anterior surface 290 of the specular object (cornea) 291. This converging beam is partially reflected by the anterior surface 290 of the test object 291. This reflected beam travels in the direction indicated by arrow 258, and impinges on lens 254 which collimates the beam. Next the beam travels to beam splitter 250, which partially reflects it in the direction of arrow 261. This partially reflected beam passes successively through polarizer 243 and beam splitter 240. This beam is then split into two beams by beam splitter 264. The transmitted beam 275 traveling in the direction indicated by arrow 276 is received and analyzed by moire deflectometer 277. Moire deflectometer 277 produces a moire deflectogram that is detected by CCD camera 278 and processed by processor 280. The beam partially reflected by beam splitter 264 is identified as beam 265 traveling in the direction indicated by arrow 266. This beam is received and analyzed by moire deflectometer 267, which produces a moire deflectogram that is detected by CCD camera 268 and processed by processor 280. Moire deflectometers 267 and 277 have their Ronchi grating pairs oriented orthogonal to each other. Let us assume that the Ronchi grooves run vertically in moire deflectometer 277 and horizontally in moire deflectometer 267. In this case, moire deflectometer 278 is sensitive to horizontal angular displacement and moire deflectometer 268 is sensitive to vertical angular displacement of an incident beam.

Now consider the portion of beam 204 partially reflected by beam splitter 215. The partially reflected beam 220 travels in the direction indicated by arrow 222. Beam 220 impinges on polarizer 223 which causes the transmitted beam to be linearly polarized in a direction orthogonal to the direction of the beam transmitted through polarizer 243. Since polarizer 243 is oriented such as to produce vertically polarized light, polarizer 223 is oriented such as to produce horizontally polarized light. The beam transmitted through polarizer 223 next passes sequentially through divergent lens 224 and convergent lens 226 before being reflected by mirror 230. The reflected beam, traveling in the direction indicated by arrow 231, impinges on beam splitter 250. The partially transmitted beam, traveling in the direction indicated by arrow 232, is focused by converging lens 254 at the front surface 290 of test object 291. This beam is partially reflected back on itself by the front surface 290 of test object 291 and travels in the direction indicated by arrow 238. This partially reflected beam passes through lens 254 and beam splitter 250 before being reflected by mirror 230. The reflected beam, traveling in the direction indicated by arrow 241, is collimated by the combined actions of lenses 254, 226, and 224. This collimated beam passes through polarizer 223 and beam splitter 215 before impinging on moire deflectometer 247. Polarizer 223 rejects any light from beam 210. The moire deflectogram produced by moire deflectometer 247 is detected by CCD camera 248 and processed by processor 280.

Lenses 224 and 254 rest on translation stages 225 and 255, respectively, that are capable of moving either in the direction or opposite to the direction of the local laser beam. That is, lens 224 may move either in direction 222 or direction 241 and lens 254 may move in either direction 232 or 238.

Prior to operation of the instrument, a calibration procedure is performed. This procedure is performed initially when the instrument is first assembled, and periodically thereafter. In the calibration procedure, standard spherical specular (reference) object with very accurately known radius of curvature approximately equal to the radius of curvature of an average human cornea, is placed with its front surface in the same location that would be occupied by the anterior surface 290 of the cornea.

Lens 254 is adjusted in position by translation stage 255, until the laser beam incident on moire deflectometers 267 and 277 are collimated. This is indicated by a horizontal pattern of moire fringes detected by camera 268 and a vertical pattern of fringes detected by camera 278. These patterns are produced by the use of Ronchi grating pairs with grooves running vertically in moire deflectometer 267 and horizontally in moire deflectometer 277. The deflectogram patterns are reversed if the Ronchi grating pairs are rotated ninety degrees. The position of the actuator that drives translation stage 254 is accurately read by means of an encoder and saved for used as a reference. Next lens 224 is adjusted in position by translation stage 225 until the laser beam incident on moire deflectometer 247 is collimated. This is indicated by a horizontal pattern (or vertical pattern depending upon the orientation of the Ronchi gratings in moire deflectometer 247) of fringes detected by camera 248. The position of the actuator that drives translation stage 225 is accurately read by means of an encoder and saved for use as a reference.

The procedure for measuring the radius of curvature and topography of a human cornea is described as follows. With the human cornea placed in position 291 of FIG. 3, the position of translation stage 255 is adjusted until nearly horizontal fringes are detected by camera 268 and nearly vertical fringes are detected by camera 278. Concurrently, translation stage 225 is adjusted until nearly horizontal fringes are detected by camera 248. The positions of the actuators that drive translation stages 225 and 255 are measured by their encoders. From these readings and the formerly recorded readings using the reference test object, the radius of curvature of the human cornea can be calculated in a straightforward manner as described in the previously referenced Utility Patent Application. The topography of the human cornea is calculated from the deflectogram patterns detected by cameras 268 and 278 in a straightforward manner also described in the previously referenced Utility Patent Application. For the convenience of the operator of the keratometer and to optimize performance, it is best if both the calibration and test procedures are automated. This can be done with the use of a computer to control the actuators, read the encoders, and interpret the data.

The previously described invention can also be used to measure the radius of curvature and topography of the posterior surface of the cornea. A weak reflection of light occurs at the posterior surface of the cornea due to the small difference in refractive index between the cornea and the aqueous substance of the eye. A correction for the refractive effect of the anterior surface of the cornea on the beam reflected from the posterior surface of the cornea must be included in the analysis.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. For use in measuring the curvature and shape of a specular object having a curved surface and a radius of curvature, a keratometer comprising:
   first, second and third moire deflectometers;
   first, second and third video cameras directed to said first, second and third moire deflectometers respectively;
   a source of collimated light;
   a beam expander coupled to said source of collimated light;
   first optical transmission means having a first beam identifier and coupling the output of said beam expander to the specular object having a first identifying characteristic such that the incident light thereon is focused at the radius of curvature of the specular object and such that the light reflected from said specular object is received by said first and second moire deflectometers;
   second optical transmission means having a second beam identifier and coupling the output of said beam expander to said specular object having a second identifying characteristic such that the incident light thereon is focused at the curved surface of the specular object.

2. A keratometer as set forth in claim 1 wherein said first and second beam identifiers include first and second polarizers having different polarization states.

3. A keratometer as set forth in claim 2 wherein said polarization states are orthogonal.

4. A keratometer as set forth in claim 1 wherein said first and second beam identifiers include first and second timesharing means energizing said first and second optical transmission means at different times.

5. A keratometer as set forth in claim 1 wherein said first and second beam identifiers include first and second modulation means operative upon said first and second optical transmission means to impose first and second modulation characteristics upon the light transmitted therethrough.

6. For use in measuring the curvature and shape of a specular object having a curved surface and a radius of curvature, a keratometer comprising:
   first, second and third moire deflectometers;
   first, second and third video cameras directed to said first, second and third moire deflectometers respectively;
   a source of collimated light;
   a beam expander coupled to said source of collimated light;
   first optical transmission means having a first beam identifier and coupling the output of said beam expander to the specular object having a first identifying characteristic such that the incident light thereon is focused at the radius of curvature of the specular object and such that the light reflected from said specular object is received by said first and second moire deflectometers;

second optical transmission means having a second beam identifier and coupling the output of said beam expander to said specular object having a second identifying characteristic such that the incident light thereon is focused at the mid-point between the radius of curvature and the curved surface of the specular object.

7. A keratometer as set forth in claim 6 wherein said first and second beam identifiers include first and second polarizers having different polarization states.

8. A keratometer as set forth in claim 6 wherein said polarization states are orthogonal.

9. A keratometer as set forth in claim 6 wherein said first and second beam identifiers includes first and second timesharing means energizing said first and second optical transmission means at different times.

10. A keratometer as set forth in claim 6 wherein said first and second beam identifiers include first and second modulation means operative upon said first and second optical transmission means to impose first and second modulation characteristics upon the light transmitted therethrough.

11. For use in measuring the curvature and shape of a specular object having a curved surface and a radius of curvature, a keratometer comprising:

first, second and third moire deflectometers;

first, second and third video cameras directed to said first, second and third moire deflectometers respectively;

a source of collimated light;

a beam expander coupled to said source of collimated light;

first optical transmission means having a first beam identifier and coupling the output of said first source of collimated light to the specular object such that the incident light thereon has a first identifying characteristic and is made divergent upon reflection therefrom and having means for receiving the divergent reflected light and restoring it to collimated light for reception by said first and second moire deflectometers;

second optical transmission means having a second beam identifier and coupling the output of said beam expander to said specular object having a second identifying characteristic such that the incident light thereon is focused at the mid-point between the radius of curvature and the curved surface of the specular object.

12. A keratometer as set forth in claim 11 wherein said first and second beam identifiers include first and second polarizers having different polarization states.

13. A keratometer as set forth in claim 12 wherein said polarization states are orthogonal.

14. A keratometer as set forth in claim 11 wherein said first and second beam identifiers include first and second time-sharing means energizing said first and second optical transmission means at different times.

15. A keratometer as set forth in claim 11 wherein said first and second beam identifiers include first and second modulation means operative upon said first and second optical transmission means to impose first and second modulation characteristics upon the light transmitted therethrough.

16. For use in measuring the curvature and shape of a specular object having a curved surface and a radius of curvature, a keratometer comprising:

first, second and third moire deflectometers;

first, second and third video cameras directed to said first, second and third moire deflectometers respectively;

a source of collimated light;

a beam expander coupled to said source of collimated light;

first optical transmission means having a first beam identifier and coupling the output of said first source of collimated light to the specular object such that the incident light thereon has a first identifying characteristic and is made divergent upon reflection therefrom and having means for receiving the divergent reflected light and restoring it to collimated light for reception by said first and second moire deflectometers;

second optical transmission means having a second beam identifier and coupling the output of said beam expander to said specular object having a second identifying characteristic such that the incident light thereon is focused at the curved surface of the specular object.

17. A keratometer as set forth in claim 16 wherein said first and second beam identifiers include first and second polarizers having different polarization states.

18. A keratometer as set forth in claim 16 wherein said polarization states are orthogonal.

19. A keratometer as set forth in claim 16 wherein said first and second beam identifiers include first and second time-sharing means energizing said first and second optical transmission means at different times.

20. A keratometer as set forth in claim 16 wherein said first and second beam identifiers include first and second modulation means operative upon said first and second optical transmission means to impose first and second modulation characteristics upon the light transmitted therethrough.

21. For use in measuring the curvature and shape of a specular object having a curved surface and a radius of curvature, a keratometer comprising:

first, second and third moire deflectometers;

first, second and third video cameras directed to said first, second and third moire deflectometers respectively;

a source of collimated light;

a beam expander coupled to said source of collimated light;

first optical transmission means having a first beam identifier and coupling the output of said beam expander to said specular object having a first identifying characteristic such that the incident light thereon is focused at the mid-point between the radius of curvature and the curved surface of the specular object;

second optical transmission means having a second beam identifier and coupling the output of said beam expander to said specular object having a second identifying characteristic such that the incident light thereon is focused at the curved surface of the specular object.

22. A keratometer as set forth in claim 21 wherein said first and second beam identifiers include first and second polarizers having different polarization states.

23. A keratometer as set forth in claim 21 wherein said polarization states are orthogonal.

24. A keratometer as set forth in claim 21 wherein said first and second beam identifiers include first and second time-sharing means energizing said first and second optical transmission means at different times.

25. A keratometer as set forth in claim 21 wherein said first and second beam identifiers include first and second modulation means operative upon said first and second optical transmission means to impose first and second modulation characteristics upon the light transmitted therethrough.

26. For use in measuring the curvature and shape of a specular object having a curved surface and a radius of curvature, a keratometer comprising:
first and second moire deflectometers;
first and second video cameras directed to said first and second moire deflectometers respectively;
a source of collimated light;
a beam expander coupled to said source;
first optical transmission means having a first beam geometry and coupling the output of said beam expander to the specular object such that the incident light thereon is processed in accordance with said first beam geometry and reflected from said specular object to be received by said first and second moire deflectometers;
second optical transmission means having a second beam geometry and coupling the output of said second source to said specular object such that the incident light thereon is processed in accordance with said second beam geometry and reflected from said specular object to be received by said second moire deflectometer; and
time share means for causing said source of light to switch between said first and second optical transmission means.

27. A keratometer as set forth in claim 26 wherein said first beam geometry includes means focusing said light at the radius of curvature and wherein said second beam geometry includes means collimating said light reflected from said specular object.

28. A keratometer as set forth in claim 26 wherein said first beam geometry includes means focusing said light at the radius of curvature and wherein said second beam geometry includes means focusing said light at the mid-point between the curved surface and the radius of curvature.

29. A keratometer as set forth in claim 26 wherein said first beam geometry includes means focusing said light at the radius of curvature and wherein said second beam geometry includes means focusing said light at the curved surface.

30. A keratometer as set forth in claim 26 wherein said first beam geometry includes means collimating said light reflected from the curved surface and wherein said second beam geometry includes means focusing said light at the mid-point between the curved surface and the radius of curvature.

31. A keratometer as set forth in claim 26 wherein said first beam geometry includes means collimating said light reflected from the curved surface and wherein said second beam geometry includes means focusing said light at the curved surface.

32. A keratometer as set forth in claim 26 wherein said first beam geometry includes means focusing said light at the radius of curvature and wherein said second beam geometry includes means focusing said light at the curved surface.

33. For use in measuring the curvature and shape of a specular object having a curved surface and a radius of curvature, a keratometer comprising:
first, second and third moire deflectometers;
first, second and third video cameras directed to said first, second and third moire deflectometers respectively;
a source of collimated light;
a beam expander coupled to said source of collimated light;
first optical transmission means having a first beam identifier and coupling the output of said beam expander to the specular object having a first identifying characteristic such that the incident light thereon is focused at the radius of curvature of the specular object and such that the light reflected from said specular object is received by said first and second moire deflectometers; and
second optical transmission means having a second beam identifier and coupling the output of said second source of collimated light to the specular object such that the incident light thereon has a second identifying characteristic and is made divergent upon reflection therefrom, said reflected, divergent light being made collimated by a collimating means and being received by said first and second moire deflectometers.

34. A keratometer as set forth in claim 33 wherein said first and second beam identifiers include first and second polarizers having different polarization states.

35. A keratometer as set forth in claim 33 wherein said polarization states are orthogonal.

36. A keratometer as set forth in claim 33 wherein said first and second beam identifiers include first and second time-sharing means energizing said first and second optical transmission means at different times.

37. A keratometer as set forth in claim 33 wherein said first and second beam identifiers include first and second modulation means operative upon said first and second optical transmission means to impose first and second modulation characteristics upon the light transmitted therethrough.

* * * * *